(12) United States Patent
Xu et al.

(10) Patent No.: US 7,732,653 B2
(45) Date of Patent: Jun. 8, 2010

(54) METHOD FOR PRODUCING GRAPHITE NANOCATALYSTS HAVING IMPROVED CATALYTIC PROPERTIES

(75) Inventors: Xuejun Xu, Westborough, MA (US); R. Terry K. Baker, Hopkinton, MA (US)

(73) Assignee: Catalytic Materials, LLC, Pittsboro, NC (US)

( * ) Notice: Subject to any disclaimer, the term of this patent is extended or adjusted under 35 U.S.C. 154(b) by 0 days.

(21) Appl. No.: 12/180,020

(22) Filed: Jul. 25, 2008

(65) Prior Publication Data

US 2009/0012337 A1   Jan. 8, 2009

Related U.S. Application Data

(60) Division of application No. 10/953,595, filed on Sep. 29, 2004, now abandoned, which is a continuation-in-part of application No. 10/712,247, filed on Nov. 13, 2003, now Pat. No. 6,913,740.

(60) Provisional application No. 60/426,198, filed on Nov. 14, 2002.

(51) Int. Cl.
   *C07C 5/42* (2006.01)
   *C07C 5/02* (2006.01)
   *C07C 5/32* (2006.01)

(52) U.S. Cl. .................. 585/443; 585/906; 585/250; 585/261; 585/379; 585/440; 585/655

(58) Field of Classification Search .................. 585/443, 585/906, 250, 261, 379, 440, 655
   See application file for complete search history.

(56) References Cited

U.S. PATENT DOCUMENTS 3,497,564 A * 2/1970 Allen et al. .................. 570/200

\* cited by examiner

*Primary Examiner*—Thuan Dinh Dang
(74) *Attorney, Agent, or Firm*—Henry E. Naylor

(57) ABSTRACT

High temperature treatment of graphite nanofibers to increase their catalytic activity. The heat treated graphite nanofiber catalysts are suitable for catalyzing chemical reactions such as oxidation, hydrogenation, oxidative-dehydrogenation, and dehydrogenation.

9 Claims, No Drawings

METHOD FOR PRODUCING GRAPHITE NANOCATALYSTS HAVING IMPROVED CATALYTIC PROPERTIES

CROSS REFERENCE TO RELATED APPLICATIONS

This is a Divisional of U.S. Ser. No. 10/953,595 filed Sep. 29, 2004, now abandoned which is based on a Continuation-in-Part of U.S. Ser. No. 10/712,247 filed Nov. 13, 2003, now U.S. Pat. No. 6,913,740, which is based on Provisional Application U.S. Ser. No. 60/426,198 filed Nov. 14, 2002.

FIELD OF THE INVENTION

This invention relates to the use of high temperature treatment of graphite nanofibers to increase their catalytic activity. The heat treated graphite nanofiber catalysts are suitable for catalyzing chemical reactions such as oxidation, hydrogenation, oxidative-dehydrogenation, and dehydrogenation.

BACKGROUND OF THE INVENTION

Much work has been done over the years in the field of heterogeneous catalysis. Such catalysts have experienced enormous commercial success in many chemical processes, particularly petroleum and petrochemical process applications. Conventional heterogeneous catalysts are typically comprised of one or more catalytically active metals, particularly Group VIII and Group VI metals on an inorganic support. The inorganic support is typically a metal oxide such as alumina, silica, alumina-silica, titania, magnesia, as well as molecular sieves. Various forms of carbon have also been suggested as being suitable as catalyst support materials. For example, U.S. Pat. Nos. 5,538,929 and 6,277,780 teach the use of a phosphorus treated activated carbon as catalyst supports. Also, U.S. Pat. No. 5,972,525 teaches solid particles comprised of carbon and metal oxides as being suitable catalyst supports. While most of the art teaches the use of conventional carbon, such as activated carbon as catalyst supports, two patents, U.S. Pat. Nos. 5,569,635 and 6,159,892 disclose the use of nano-size cylindrical carbon "fibrils" as catalyst supports. Various catalytically active metals, preferably noble and non-noble Group VIII metals, such as Fe and Pt, are deposited onto the fibril support material. Metal oxides, such as $Fe_2O_3$ can also act as a catalyst when deposited onto the carbon fibrils.

While it has been known for many years that both macro and nano-size carbon particles are suitable support materials for certain types of catalysts, it has not been known that certain types of graphitic nanofibers have unique and unexpected catalytic properties themselves, without the addition of a catalytically active metal. In co-pending application, U.S. Ser. No. 10/712,247, it is disclosed that graphitic nanofibers comprised of a plurality of graphite sheets aligned in directions parallel, perpendicular, or at an angle to the longitudinal axis of the nanofiber are suitable for catalyzing a variety of chemical reactions. It has unexpectedly been found by the inventors hereof that if the graphite nanofibers in which the graphite sheets are oriented perpendicular, or at an angle, to the longitudinal axis are initially treated at high temperatures then their subsequent catalytic performance is unexpectedly enhanced over that of the corresponding untreated materials.

SUMMARY OF THE INVENTION

A catalytic process selected from oxidation, hydrogenation, dehydrogenation, oxidative-hydrogenation, and oxidative-dehydrogenation which is catalyzed by a catalyst composition comprised of graphitic nanofibers which nanofibers are comprised of a plurality of graphite platelets aligned perpendicular, or at an angle to the longitudinal axis of the nanostructure and wherein at least about 50% of the edge sites of said nanofibers are exposed, wherein said graphite nanofibers, prior to use in said catalytic process are heat treated in the presence of an inert gas at temperatures from about 2300° C. to about 3000° C.

In another preferred embodiment these high temperature treated graphite nanofibers can be used as support media for metal particles.

DETAILED DESCRIPTION OF THE INVENTION

The catalysts of the present invention are graphite nanofibers. These graphite nanofibers are themselves comprised of a plurality of graphite platelets, also sometimes called graphite sheets, that are aligned, perpendicular, or at an angle to the longitudinal (growth) axis of the nanofiber. By "at an angle" we mean that the graphite platelets are aligned so that they are neither parallel nor perpendicular to the longitudinal axis of the nanofiber. For example they can be from about 1° to about 89°, preferably from about 10° to about 80°, more preferably from about 20° to about 70°, and most preferably from about 30° to about 60° with respect to the longitudinal axis of the nanofiber. In the case where the graphitic sheets are oriented substantially perpendicular to the growth axis, the carbon nanofibers are sometimes referred to as "platelet" nanofibers. In the case where the graphitic sheets are oriented at an angle to the growth axis, the nanofibers are sometimes referred to as "herringbone" nanofibers. The term "carbon" is sometimes used interchangeably with "graphite" herein and the word "nanostructure" is sometimes used interchangeably with "nanofiber" herein.

The graphite nanofibers of the present invention are novel materials having a unique set of properties that include: (i) a surface area from about 20 to 50 $m^2/g$, preferably from about 30 to 45 $m^2/g$, more and most preferably from about 35 to 40 $m^2/g$, which surface area is determined by $N_2$ adsorption at −196° C.; (ii) a crystallinity from about 5% to about 100%, preferably from about 50% to 100%, more preferably from about 75% to 100%, most preferably from about 90% to 100%, and ideally substantially 100%; (iii) an average pore size from about 10 to 15 nm, most preferably from about 11 to 13 nm and ideally 12 nm; (iv) interstices of about 0.335 nm to about 0.40 nm, preferably about 0.335 nm; and (v) unexpectedly high catalytic properties for certain chemical reactions. The interstices are the distance between the graphite platelets. The over all shape of the nanofibers can be any suitable shape. Non-limiting examples of preferred shapes include straight, branched, twisted, spiral, helical, and coiled.

The graphite nanofiber catalysts of the present invention can be catalytically grown from suitable unsupported metal powders in a carbon containing atmosphere. A carbon-containing compound is decomposed in the presence of the metal catalyst at temperatures from about 450° C. to about 800° C., preferably from about 550° C. to about 700° C. It is also preferred that hydrogen be present during the decomposition of the carbon-containing compound. The graphite nanofibers of the present invention are treated in an inert gas environment to a temperature from about 1800° C. to about 3000° C., preferably from about 2300° C. to about 3000° C. Preferred inert gases are helium and argon with helium being more preferred. This high temperature heat treatment is what gives the graphite nanofibers of the present invention their unexpected improved catalytic properties when compared to similar graphite nanofibers that were not subjected to high temperature heat treatment.

Metal powdered catalysts suitable for growing the carbon nanofibers of the present invention include single metals, as well as alloys and multi-metallics. If the metal catalyst is a single metal then it is preferably a Group VIII metal selected from Fe, Ni, and Co. If the catalyst is an alloy or multi-metallic material, then it is preferred that it be comprised of a first metal component that will be one or more Group VIII metals and a second metal that is preferably one or more Group IB metals, such as Cu, Ag, and Au. Preferred are Cu and Ag with Cu being the most preferred. It will be understood that Zn can be used in place of one or more of the Group VIII metals. The Group IB metals are present in an amount ranging from about 0.5 to 99 at. % (atomic %). For example the catalyst can contain up to about 99 at. %, even up to about 70 at. %, or even up to about 50 at. %, preferably up to about 30 at. %, more preferably up to about 10 at. %, and most preferably up to about 5 wt. % of Group IB metal with the remainder being a Group VIII metal, preferably nickel or iron, more preferably iron.

Catalysts having a high copper content (70 at. % to 99 at. %) will typically generate nanofibers that are predominantly helical or coiled, in overall shape, and which have a relatively low crystallinity (from about 5 to 25%). Lower concentrations of copper, e.g., 0.5 to 30 at. % have a tendency to produce spiral and branched nanofibers, whereas a catalyst with about 30 to 70 at. %, preferably 30 to 50 at. % copper will produce predominantly branched nanofibers. A third metal can also be present. There is no limitation with respect to what the particular third metal can be as long as it is not deleterious to the desired end product nanofiber. It is preferred that the third metal, if used, be selected from the group consisting of Ti, W, Sn and Ta. When a third metal is present, it is substituted for up to about 20 at. %, preferably up to about 10 at. %, and more preferably up to about 5 at. %, of the second metal. It is preferred that the catalyst be comprised of Cu in combination with Fe, Ni, or Co. More preferred is Cu in combination with Fe and/or Ni from an economic point of view. A catalyst of which Fe is used in place of some of the Ni would be less expensive than a catalyst comprised of Cu in combination with only Ni. Preferred catalysts for producing graphite nanofibers wherein the platelets are substantially perpendicular to the longitudinal axis of the nanofiber are Fe and Fe/Cu multi-metallics. Preferred catalysts for producing graphite nanofibers wherein the graphite platelets are at an angle, other than 90 degrees, from the growth axis, are Fe, Fe/Cu multi-metallics, Fe/Ni multi-metallics, and Ni/Cu multi-metallics. The preferred temperature range for growing "platelet" graphite nanofibers is from about 550° to about 650° C., preferably from about 575° to about 625° C. The preferred temperature range for growing the angled "herringbone" graphite nanofibers is from about 550° to about 580° C.

Any suitable method can be used to produce the powdered metal catalyst for growing the graphite nanocatalysts of the present invention. As previously mentioned, it is most preferred in the practice of the present invention that the graphite nanocatalysts be grown from unsupported metallic powders. A preferred method for preparing suitable unsupported metal catalytic powders is the use of colloidal techniques for precipitating them as metal oxides, hydroxides, carbonates, carboxylates, nitrates, etc. Such a process typically involves dissolving salts of each metal of the catalyst in an appropriate solvent, preferably water. A suitable precipitating agent, such as an ammonium carbonate, ammonium bicarbonate or ammonium hydroxide is added to the solution, thereby causing the metal to precipitate out as the corresponding metal carbonate or hydroxide. The precipitate is then dried at a temperature greater than about 100° C., preferably from about 105° C. to about 120° C., and more preferably at about 110° C. After drying, the precipitate is mixed with a suitable dispersing agent and calcined at a temperature from about 200° to 400° C., preferably from about 200° to about 300° C., thereby converting the individual metals to their respective oxide form. The milled metal powder mixture can then heated, in a hydrogen-containing atmosphere, at a temperature from about 400° to about 600° C., preferably from about 450° to 550° C., for an effective amount of time, to produce the catalyst in its metallic state. By effective amount of time, we mean that amount of time needed to reduce substantially all of the metal oxides to the respective metal or alloy having a suitable particle size. A typical amount of time will generally be from about 15 to 25 hours. Suitable particle sizes are from about 2.5 nm to about 150 nm, preferably from about 2.5 nm to about 100 nm, and more preferably from about 2.5 nm to about 20 nm. Following this treatment the chemically reduced catalyst is cooled to about room temperature in a helium environment before being passivated in a 2% oxygen/helium mixture for 1 hour at about room temperature (24° C.).

Salts of the catalytic metal used for growing the graphitic nanofiber catalysts of the present invention are salts that are soluble in water, organic solvents, and diluted mineral acids. Non-limiting examples of water-soluble salts suitable for use herein include nitrates, sulfates and chlorides. Non-limiting examples of preferred salts soluble in organic solvents, which are suitable for use herein, include formates, acetates, and oxalates. Non-limiting examples of organic solvents that are suitable for use herein include alcohols, such as methanol, ethanol, propanol, and butanol; ketones, such as acetone; acetates and esters; and aromatics, such as benzene and toluene.

Carbon-containing compounds suitable for creating an atmosphere for the growth of the graphitic nanocatalysts of the present invention are compounds composed mainly of carbon atoms and hydrogen atoms, although carbon monoxide can also be used. The carbon-containing compound, which is typically introduced into the heating zone in gaseous form, will generally have no more than 8 carbon atoms, preferably no more than 6 carbon atoms, more preferably no more than 4 carbon atoms, and most preferably no more than 2 carbon atoms. Non-limiting examples of such compounds include CO, methane, ethane, ethylene, acetylene, propane, propylene, butane, butene, butadiene, pentane, pentene, cyclopentadiene, hexane, cyclohexane, benzene, and toluene. Combinations of gases are preferred, particularly carbon monoxide and ethylene.

It may be desirable to have an effective amount of hydrogen present in the heating, or growth, zone during nanostructure growth. Hydrogen serves two complementary functions. For example, on the one hand it acts as a reconstruction agent for the catalyst, suppresses the formation of metal carbide that results in deactivation and on the other hand it hydrogasifies, or causes carbon burn-off, of the carbon structure. By an effective amount, we mean that minimum amount of hydrogen that will maintain a clean catalyst surface (free of carbon residue), but not so much that will cause excessive hydrogasification, or burn-off, of carbon from the nanostructures and/or substrate structure, if present. Generally, the amount of hydrogen present will range from about 5 to 40 vol. %, preferably from about 10 to 30 vol. %, and more preferably from about 15 to 25 vol. %. For some catalyst systems, such as Cu:Fe, the hydrogasification reaction is relatively slow, thus, an effective amount of hydrogen is needed to clean the catalyst in order to keep it clean of carbon residue and maintain its activity. For other catalyst systems, such as Cu:Ni, where the activity is so high that excessive hydrogasification occurs, even at relatively low levels of hydrogen, little, if any, hydrogen is needed in the heating zone. A Cu:Ni catalyst is so active that it utilizes essentially all of the carbon deposited thereon to grow nanofibers, and thus, there is generally no carbon residue to clean off.

After the carbon nanofibers are grown, it is required to heat the final structure in an inert gas at temperatures up to about 3000° C., preferably from about 1800° C. to about 3000° C., and more preferably from about 2300° C. to about 3000° C. Under these conditions, the surface area of the nanofibers are decreased because up to 50% of the adjacent edges of the nanofibers undergo a sealing action to form the type of modified structure of the present invention.

As previously mentioned, the graphite nanofiber catalysts of the present invention are suitable for catalyzing a variety of chemical reactions. Non-limiting examples of chemical reactions that can be catalyzed with the graphite nanofiber catalysts of the present invention include oxidation, hydrogenation, oxidative-dehydrogenation, and dehydrogenation. One preferred oxidative dehydrogenation reaction is the conversion of ethylbenzene to styrene.

Below is a first table setting forth preferred hydrogenation reactions along with the typical catalytic metal used and reaction conditions employed.

HYDROGENATION REACTIONS

| Reaction | Catalyst | Temperature Range (° C.) | Pressure (atm) |
|---|---|---|---|
| Benzene to cyclohexane | Ni | 180-230 | 20-50 |
| Nitrobenzene to Aniline | Pd, Pt | 50-150 | 1-5 |
| Reductive alkylation of nitroaromatics | Pt | ~50 | ~1 |
| Nitriles to amines | Co, Ru, Ni | 80-200 | 20-170 |
| Hydrogenation of fats & oils | Ni | 120-175 | 1-2 |

Below is a first table setting forth preferred oxidation reactions along with the typical catalytic metal used and reaction conditions employed.

OXIDATION REACTIONS

| Reaction | Catalyst | Temperature Range (° C.) | Pressure (atm) |
|---|---|---|---|
| Sulfur dioxide to sulfuric acid | $V_2O_5/K_2O$ | 420-480 | ~1 |
| Ethylene to ethylene oxide | Ag | 200-250 | ~8 |
| Ethylene to vinyl acetate | Pd | 10-130 | 30 |
| Propylene to acrolein | $Bi_2O_3/Mo_2O_3$ | 320-430 | 2 |

It is evident that a number of factors can exert an impact on the ultimate performance of the carbon nanofiber catalysts. When dealing with active carbons one generally considers the textural characteristics of the solid with particular emphasis being placed on the surface area and the pore size distribution. Unfortunately, the small pore size of active carbons appears to be responsible for obstructing desorption of the styrene, which blocks surface sites and eventually poisons the catalyst. A further shortcoming of active carbons is their propensity to undergo gasification at about 550° C., a temperature close to that where the oxidative dehydrogenation reaction is conducted. On the other hand, graphitic materials are more resistant to attack by oxygen. As a consequence, such carbons are stable at 550° C. and would not be susceptible to poisoning by adsorption of styrene molecules.

The catalytic performance of the heat-treated graphite nanofibers is dependent upon the electrical conductivity of the materials. This property can be enhanced via intercalation with various electron donor and acceptor molecules. Inorganic molecules and compounds that can form intercalation compounds with the graphite nanofibers include Li, Na, K, Rb, Cs, $Br_2$, $Cl_2$, $F_2$, ICl, $ICl_3$, $H_2SO_4$, $HNO_3$, $H_2SeO_4$, $HClO_4$, $H_3PO_4$, $H_4P_2O_7$, $H_3AsO_4$, HF, $CrO_2Cl_2$, $CrO_2F_2$, $UO_2Cl_2$, FeCl, $CuCl_2$, $BCl_3$, $AlCl_3$, $CoCl_3$, $RuCl_3$, $RhCl_3$, $PdCl_4$, $PtCl_4$, $Cr_2O_3$, $Sb_2O_3$, $MoO_3$, $Sb_2S_3$, CuS, $FeS_2$ $Cr_2S_3$, $V_2S_3$ and $WS_2$.

The present invention will be illustrated in more detail with reference to the following examples, which should not be construed to be limiting in scope of the present invention.

EXAMPLES

Materials

The "platelet" graphitic nanofibers (P-GNF) used in these examples were prepared from the decomposition of a carbon monoxide/hydrogen mixtures over a copper-iron powdered catalyst at 600° C. Prior to use, all nanofibers were treated in dilute mineral acid for a period of one week to remove associated metal catalyst particles. Samples of these nanofibers were subsequently treated in argon for 30 minutes at either 1800° C. or 2330° C. Examination of these heat-treated materials by high-resolution transmission electron microscopy revealed that many of the adjacent edges had undergone a sealing action by generating loops at the exposed regions The gases used in these examples were carbon monoxide (99.9%), ethylene (99.95%); hydrogen (99.999%), helium (99.99%) and argon (99.99%) were purchased from Air Products and dried before use. Reagent grade iron nitrate, cobalt nitrate, nickel nitrate, copper nitrate and magnesium oxide were used in the preparation of catalysts for carbon nanofiber growth and were obtained from Fisher Scientific.

Example 1

The oxidative dehydrogenation of ethylbenzene to styrene was carried out in a packed bed tubular quartz flow reactor system. The flow rates of the gaseous reactants, oxygen and helium, were regulated by MKS mass flow controllers. Ethylbenzene (EB) was introduced into the reactor using a syringe pump. The inlet and outlet gas analyses were performed on-line using a gas chromatograph equipped with thermal conductivity detectors (TCD) and flame ionization detectors (FID) detectors. The performance of each catalyst sample was determined from the conversion of EB, the selectivity to styrene (ST) and the resulting yield of styrene. These values were calculated according to the following equations:

$$EB_{conversion} = \frac{n_{EB_{in}} - n_{EB_{ex}}}{n_{EB_{in}}} \quad (1)$$

$$ST_{selectivity} = \frac{n_{ST_{ex}}}{n_{EB_{in}} - n_{EB_{ex}}} \quad (2)$$

$$ST_{yield} = \frac{n_{ST_{ex}}}{n_{EB_{ex}}} \quad (3)$$

where, n is the number of moles of a given compound, "in" and "ex" refer to inlet and exit, respectively.

In this series of experiments the behavior of high temperature treated graphite nanofibers for synthesis of styrene as a function of reaction temperature was investigated. Table 1 below shows the behavior of the modified platelet graphite nanofibers (P-GNF) that was treated at 2330° C. in argon for 30 minutes. The reaction conditions were as follows: mole ratio $O_2/EB=1.4$, EB flow rate=$9.33 \times 10^{-6}$ mol/min, He=9.8 cc/min, catalyst weight=40.6 mg. In each case, the data were taken after 22 hours on stream. Examination of these data shows that as the reaction temperature is progressively raised there is a corresponding increase in the EB conversion, reaching a maximum level at about 600° C. On the other hand, the optimum selectivity to the desired product, styrene, is achieved at 450° C. and the maximum yield of styrene occurs at 575° C.

TABLE 1

| Temperature (° C.) | EB Conversion (%) | ST Selectivity (%) | ST Yield (%) |
| --- | --- | --- | --- |
| 450 | 23.5 | 100.0 | 23.7 |
| 475 | 34.3 | 93.6 | 32.1 |
| 500 | 47.7 | 92.8 | 44.2 |
| 547 | 69.6 | 76.5 | 53.3 |
| 575 | 73.7 | 78.2 | 57.7 |
| 600 | 80.7 | 69.9 | 56.4 |
| 625 | 76.9 | 70.1 | 53.8 |
| 650 | 76.4 | 61.6 | 47.1 |

Example 2

In this set of experiments the heat-treated P-GNFs described above were reacted in various ethylbenzene/oxygen mixtures at 500° C. Other reaction conditions were as follows: EB flow rate=$9.33 \times 10^{-6}$ mol/min, He=9.8 cc/min, catalyst weight=40.6 mg and the data presented in Table 2 were taken after 22 hours on stream. Inspection of these data shows that as the $O_2/EB$ ratio is increased there is a concomitant increase in the conversion of the hydrocarbon. However, as the $O_2/EB$ ratio is raised above 1.0 the selectivity to styrene declines. The optimum conditions for the process appear to be an $O_2/EB$ ratio of about 1.0.

TABLE 2

| $O_2/EB$ Mole Ratio | EB Conversion (%) | ST Selectivity (%) | ST Yield (%) |
| --- | --- | --- | --- |
| 0.5 | 25.8 | 99.9 | 25.8 |
| 0.86 | 39.1 | 100.0 | 40.4 |
| 1.0 | 43.8 | 99.7 | 43.6 |
| 1.4 | 47.7 | 92.8 | 44.2 |
| 1.9 | 48.8 | 91.2 | 44.1 |

Example 3

This series of experiments was conducted to establish the activity maintenance and selectivity pattern of the modified P-GNF catalyst for the ethylbenzene oxidative dehydrogenation reaction at 547° C. as a function of time. Other reaction conditions were as follows: mole ratio $O_2/EB=0.86$, EB flow rate=$9.33 \times 10^{-6}$ mol/min, He=9.8 cc/min, catalyst weight=40.6 mg.

TABLE 3

| Reaction Time (h) | EB conversion (%) | ST selectivity (%) | ST yield (%) |
| --- | --- | --- | --- |
| 0.50 | 24.6 | 50.7 | 12.5 |
| 4.62 | 41.9 | 81.7 | 34.2 |
| 5.10 | 41.2 | 99.3 | 40.9 |
| 6.65 | 42.7 | 100.0 | 42.0 |
| 9.95 | 45.8 | 100.0 | 46.2 |
| 10.97 | 47.5 | 100.0 | 48.3 |
| 12.48 | 51.0 | 94.7 | 48.3 |
| 15.80 | 51.2 | 93.9 | 48.1 |
| 18.30 | 53.8 | 93.2 | 50.1 |
| 22.73 | 53.9 | 89.8 | 48.3 |

Examination of the data presented in Table 3 shows that following an induction period of about 5 hours, the catalytic activity of the modified P-GNFs for ethylbenzene conversion actually increases with time and maintains a very high selectivity towards the formation of the desired product, styrene for an extended period of time. This behavior is to be contrasted with that of the corresponding P-GNFs not heat-treated (Table 4), which undergoes deactivation after a relatively short time on stream while maintaining the selectivity for styrene production.

Example 4

A comparison study was carried out using P-GNFs not heat-treated and reacted under the same conditions as those used in Example 3. The reaction conditions were as follows: reaction temperature 547° C., mole ratio $O_2/EB=0.86$, EB flow rate=$9.33 \times 10^{-6}$ mol/min, He=9.8 cc/min, catalyst weight=40.4 mg.

TABLE 4

| Reaction Time (h) | EB conversion (%) | ST selectivity (%) | ST yield (%) |
| --- | --- | --- | --- |
| 0.25 | 59.9 | 85.5 | 51.2 |
| 1.28 | 48.9 | 87.1 | 42.6 |
| 1.82 | 46.7 | 83.8 | 39.2 |
| 2.35 | 43.6 | 88.3 | 38.5 |
| 2.90 | 38.2 | 90.1 | 37.8 |
| 3.42 | 37.8 | 90.7 | 36.7 |
| 3.93 | 40.3 | 87.6 | 35.3 |
| 4.47 | 40.1 | 86.7 | 34.8 |
| 9.63 | 31.6 | 82.4 | 26.0 |

Inspection of the data given in Table 4 shows that the catalytic activity declines over the reaction period while the selectivity pattern remains unchanged. Clearly the performance of this system is inferior to that displayed by the high-temperature treated P-GNFs.

Example 5

In this set of experiments the performance of the modified P-GNFs catalyst for the ethylbenzene oxidative dehydrogenation reaction at 500° C. as a function of time was investigated.

TABLE 5

| Reaction Time (h) | EB conversion (%) | ST selectivity (%) | ST yield (%) |
| --- | --- | --- | --- |
| 0.57 | 38.3 | 100.0 | 39.9 |
| 1.68 | 44.5 | 95.3 | 42.4 |
| 2.73 | 42.0 | 100.0 | 43.1 |
| 3.22 | 43.5 | 100.0 | 43.6 |
| 3.72 | 45.2 | 94.6 | 42.8 |

TABLE 5-continued

| Reaction Time (h) | EB conversion (%) | ST selectivity (%) | ST yield (%) |
|---|---|---|---|
| 4.27 | 43.7 | 99.4 | 43.5 |
| 4.73 | 44.4 | 100.0 | 45.2 |
| 5.25 | 41.3 | 100.0 | 43.5 |
| 6.00 | 41.1 | 100.0 | 42.3 |
| 16.00 | 41.9 | 100.0 | 42.5 |

The catalyst had been previously utilized at higher temperature and was therefore already in an activated state. Other reaction conditions were as follows: mole ratio $O_2/EB=0.86$, EB flow rate=$9.33\times10^{-6}$ mol/min, He=9.8 cc/min, catalyst weight=40.6 mg. Examination of the data given in Table 5 reveals that over a period of 16 hours the catalyst performance remains relatively stable. It is also apparent that under these conditions that the high-temperature treated P-GNF catalyst exhibits an exceedingly high selectivity towards styrene production and moreover, this high level is maintain for the entire period of the reaction.

Example 6

In a further series of experiments the catalytic behavior of a commercial carbon black, XC72 was investigated. This material is available from Cabot Corporation and has a surface area of 230 $m^2/g$ and an average pore size of 5.2 nm. The conditions used were the same as those used in Example 5. The oxidative dehydrogenation of ethylbenzene was carried out at 500° C. for an extended period of time. Other reaction conditions were as follows: mole ratio $O_2/EB=0.86$, EB flow rate=$9.33\times10^{-6}$ mol/min, He=9.8 cc/min, catalyst weight=40.5 mg. From the results given in Table 6 it is evident that the catalyst exhibits a progressive decrease in activity as the reaction proceeds. Furthermore, the selectivity towards styrene formation also declines with time on stream. A comparison of the performance of this type of carbon with the high-temperature treated P-GNFs shows that the latter material exhibits a superior performance.

TABLE 6

| Reaction Time (h) | EB conversion (%) | ST selectivity (%) | ST yield (%) |
|---|---|---|---|
| 0.40 | 41.6 | 90.3 | 37.6 |
| 1.48 | 35.6 | 98.9 | 35.2 |
| 3.52 | 35.1 | 94.2 | 33.1 |
| 5.23 | 33.1 | 98.8 | 32.7 |
| 9.82 | 31.8 | 92.1 | 29.3 |
| 12.53 | 35.5 | 80.3 | 28.5 |

Example 7

The data given in Table 7 shows the comparison of the performance of various materials, including the current commercial system based on Fe, Cr, K oxides, for the catalyzed oxidative dehydrogenation of ethylbenzene at 500° C. Other reaction conditions were as follows: mole ratio $O_2/EB=0.86$, EB flow rate=$9.33\times10^{-6}$ mol/min, He=9.8 cc/min, catalyst weight=40.5 mg. The data were taken 17 hours after the start of the reaction.

TABLE 7

| Catalyst | (%) EB conversion | (%) ST selectivity | (%) ST yield | S.A. ($m^2/g$) | Pore Size (nm) |
|---|---|---|---|---|---|
| P-GNF 2330° | 39.1 | 100.0 | 40.4 | 40 | 13.2 |
| P-GNF 1800° | 34.2 | 100.0 | 34.7 | 50 | 11.8 |
| P-GNF | 35.1 | 94.1 | 33.0 | 80 | 6.3 |
| XC-72 | 34.6 | 75.5 | 29.3 | 230 | 5.2 |
| Fe, Cr, K oxides | 6.9 | 75.9 | 5.2 | 4.4 | 4.0 |

Examination of the results shows some significant features and highlights the superior performance of the P-GNFs that had been treated in argon at 2330° C., which is significantly better than that of the same type of GNF that had been heated to 1800° C. While both of these materials exhibited a 100% selectively towards styrene, it is the generation of a higher pore size in the former that appears to be the critical factor. Indeed, when one considers all the data there appears to be a direct correlation between pore size and catalytic performance. In sharp contrast, the magnitude of the surface area of the materials does not have an impact on the catalytic behavior.

The electrical conductivity of high temperature treated "platelet" graphite nanofibers of the present invention were enhanced by the interaction of concentrated nitric acid at 90° C. Under these conditions $HNO_3$ species intercalates between the exposed graphite edge sites to initially form a compound having the formula, $C_6HNO_3$ and after continued uptake, the intercalation compound, $C_{12}HNO_3$ is produced. The achievement of this final stage compound resulted in an enhancement of a factor of 20 over that of the pristine material. Furthermore, these compounds are relatively stable in air. The formation of an intercalation compound was confirmed by X-ray diffraction analysis in which the expansion of the $d_{002}$-spacing was measured.

What is claimed is:

1. A catalytic chemical reaction selected from oxidation, hydrogenation, dehydrogenation, oxidative-hydrogenation, and oxidative-dehydrogenation which is catalyzed by a catalyst composition comprised of graphitic nanofibers which nanofibers are comprised of a plurality of graphite platelets aligned at an angle from about 1° to about 90° with respect to the longitudinal axis of the nanofibers and which nanofibers have a crystallinity greater than about 90%, which method comprises heat treating said nanofibers in an inert gas environment at temperatures from about 2300° C. to about 3000° C.

2. The catalytic chemical reaction of claim 1 which is a oxidative-hydrogenation reaction.

3. The catalytic chemical reaction of claim 2 which is the oxidative-hydrogenation reaction of ethylbenzene to styrene.

4. The catalytic chemical reaction of claim 1 wherein the platelets are aligned substantially 90° with respect to the longitudinal axis of the nanofiber.

5. The catalytic chemical reaction of claim 1 wherein the platelets are aligned at angle from about 30° to about 60° with respect to the longitudinal axis of the nanofibers.

6. The catalytic chemical reaction of claim 1 wherein the inert gas is selected from helium and argon.

7. The catalytic chemical reaction of claim 3 wherein the platelets are aligned substantially 90° with respect to the longitudinal axis of the nanofiber.

8. The catalytic chemical reaction of claim 3 wherein the platelets are aligned at angle from about 30° to about 60° with respect to the longitudinal axis of the nanofibers.

9. The catalytic chemical reaction of claim 3 wherein said graphitic nanofibers are intercalated with an intercalation component selected from the group consisting of Li, Na, K, Rb, Cs, $Br_2$, $Cl_2$, $F_2$, ICl, $ICl_3$, $H_2SO_4$, $HNO_3$, $H_2SeO_4$, $HClO_4$, $H_3PO_4$, $H_4P_2O_7$, $H_3AsO_4$, HF, $CrO_2Cl_2$, $CrO_2F_2$, $UO_2Cl_2$, FeCl, $CuCl_2$, $BCl_3$, $AlCl_3$, $CoCl_3$, $RuCl_3$, $RhCl_3$, $PdCl_4$, $PtCl_4$, $Cr_2O_3$, $Sb_2O_3$, $MoO_3$, $Sb_2S_3$, CuS, $FeS_2$ $Cr_2S_3$, $V_2S_3$ and $WS_2$.

* * * * *